United States Patent
Koseoglu et al.

(10) Patent No.: US 11,091,701 B2
(45) Date of Patent: Aug. 17, 2021

(54) CONVERSION OF OLEFINIC NAPHTHAS BY HYDRATION TO PRODUCE MIDDLE DISTILLATE FUEL BLENDING COMPONENTS

(71) Applicant: Saudi Arabian Oil Company, Dhahran (SA)

(72) Inventors: Omer Refa Koseoglu, Dhahran (SA); Ali Sawan, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/244,444

(22) Filed: Jan. 10, 2019

(65) Prior Publication Data

US 2020/0224107 A1    Jul. 16, 2020

(51) Int. Cl.
| | |
|---|---|
| *C10G 35/06* | (2006.01) |
| *B01J 35/02* | (2006.01) |
| *B01J 35/10* | (2006.01) |
| *C10G 35/14* | (2006.01) |
| *C10G 35/24* | (2006.01) |

(52) U.S. Cl.
CPC ............ *C10G 35/06* (2013.01); *B01J 35/023* (2013.01); *B01J 35/1014* (2013.01); *B01J 35/1061* (2013.01); *C10G 35/14* (2013.01); *C10G 35/24* (2013.01); *C10G 2300/1096* (2013.01); *C10G 2300/202* (2013.01); *C10G 2300/307* (2013.01); *C10G 2300/4006* (2013.01); *C10G 2300/4081* (2013.01); *C10G 2400/04* (2013.01); *C10G 2400/08* (2013.01)

(58) Field of Classification Search
CPC ........ C10G 35/06; C10G 35/14; C10G 35/24; C10G 2300/307; C10G 2300/4006; C10G 2300/4081; C10G 2400/04; C10G 2400/08; B01J 35/023; B01J 35/1014; B01J 35/1061

See application file for complete search history.

(56) References Cited

U.S. PATENT DOCUMENTS

| | | |
|---|---|---|
| 2,987,465 A | 6/1961 | Johanson |
| 3,197,288 A | 7/1965 | Johanson |
| 4,499,313 A | 2/1985 | Okumura et al. |

(Continued)

FOREIGN PATENT DOCUMENTS

| | | |
|---|---|---|
| WO | 86/05776 A1 | 10/1986 |
| WO | 2012/076758 A2 | 6/2012 |

OTHER PUBLICATIONS

Sharma, M.M. (1995) Reactive & Functional Polymers, 26, 3-23.*

*Primary Examiner* — Brian A McCaig
(74) *Attorney, Agent, or Firm* — Abelman, Frayne & Schwab

(57) ABSTRACT

A process for the production of middle distillates by the catalytically promoted hydration of olefinic compounds having a carbon number ranging from 7 to 14 to convert the olefins to the corresponding mixed alcohols having a higher boiling point that is in the diesel range, the process being conducted in a continuous stirred tank reactor, e.g., an ebullated-bed reactor, utilizing catalysts that include soluble homogeneous acidic compounds and solid heterogeneous compounds such as resins, and amorphous or structured metal oxides containing elements selected from IUPAC Groups 4-10, 13 and 14, and having Lewis or Bronsted acid sites.

25 Claims, 6 Drawing Sheets

(56) References Cited

U.S. PATENT DOCUMENTS

| | | |
|---|---|---|
| 4,990,239 A | 2/1991 | Derr, Jr. et al. |
| 5,102,428 A | 4/1992 | Owen et al. |
| 5,233,101 A * | 8/1993 | Harandi ............. C10G 57/00 568/897 |
| 5,243,102 A | 9/1993 | Marker et al. |
| 5,258,560 A | 11/1993 | Marker |
| 5,362,377 A | 11/1994 | Marker |
| 5,395,981 A | 3/1995 | Marker |
| 5,407,654 A | 4/1995 | Tissler et al. |
| 5,578,195 A | 11/1996 | Tissler et al. |
| 5,696,043 A | 12/1997 | Tissler |
| 5,711,869 A | 1/1998 | Tissler |
| 6,824,574 B2 | 11/2004 | O'Rear et al. |
| 7,148,387 B2 | 12/2006 | Takahashi |
| 7,402,187 B2 | 7/2008 | O'Rear et al. |
| 7,482,497 B2 | 1/2009 | Hassan et al. |
| 8,344,188 B2 | 1/2013 | Kharas |
| 8,354,563 B2 | 1/2013 | Kharas |
| 8,357,826 B2 | 1/2013 | Kharas |
| 8,558,036 B2 | 10/2013 | Xu |
| 2005/0039385 A1 | 2/2005 | O'Rear et al. |
| 2005/0119111 A1 | 6/2005 | Ramprasad et al. |
| 2006/0270866 A1 | 11/2006 | Sapienza et al. |
| 2008/0250705 A1 | 10/2008 | O'Rear et al. |
| 2010/0005709 A1 | 1/2010 | Bradin |
| 2010/0197978 A1* | 8/2010 | Dakka ............. B01J 21/066 568/900 |
| 2011/0028573 A1 | 2/2011 | Hassan et al. |
| 2012/0117862 A1* | 5/2012 | Xu ............. C07C 29/04 44/452 |
| 2015/0225320 A1* | 8/2015 | Shaik ............. C07C 29/04 44/452 |
| 2016/0115107 A1* | 4/2016 | Arjah ............. C07C 29/04 568/895 |

\* cited by examiner

CONVERSION OF OLEFINIC NAPHTHAS BY HYDRATION TO PRODUCE MIDDLE DISTILLATE FUEL BLENDING COMPONENTS

FIELD OF THE INVENTION

The invention is directed to an integrated refinery process and apparatus for the production of middle distillates through the hydration of olefinic naphtha, and more specifically to convert gasoline range hydrocarbons into diesel range components.

BACKGROUND OF THE INVENTION

Middle distillates, which include residential, commercial and industrial heating oil, as well as serving as the primary commercial transportation fuel source, make up approximately 30 percent of the global market for refined products. The demand for middle distillates has steadily increased worldwide and continues to grow at a higher rate than for any other refined petroleum product.

In the United States, middle distillates are vital to the development of the country's economic infrastructure since they serve as the primary fuel source for the transportation of goods throughout the country. Despite the dominance of gasoline as the primary United States passenger-vehicle fuel, diesel fuel has been the primary driver of recent growth in the petroleum markets. Prior to the economic downturn from 2007 to 2009, United States diesel fuel demand was growing by more than 2 percent annually, compared to gasoline demand growth of 1.2 percent. As the United States economy recovers from its economic downturn, diesel is expected to once again resume its role as a primary energy component supporting economic expansion and development.

Advanced diesel refining technology that was introduced in 2007 has produced clean diesel fuel with an ultra-low sulfur content of <10 ppmw and has also reduced emissions of particulate matter and nitrogen oxides by more than 98 percent as compared to emissions from heavy-duty truck models of the early 2000's. Moreover, the technology has resulted in the development and commercialization of high performance diesel cars, trucks, and SUVs that are cleaner and quieter than previous models.

With the introduction of new fuel economy mandates, diesel fuel is in a position to assume an even greater role in the United States transportation market. To address rising consumer demand for diesel fuel, retailers have increased availability and diesel fuel is now available at more than half of all United States retail filling stations. In the near future, refineries will likely be forced to either invest in conversion processes which increase the proportional yield of middle distillates or find alternative processes to produce the middle distillates required to meet the anticipated demand.

With the increasing demand for middle distillates, many new refineries utilize hydrocracking rather than fluid catalytic cracking (FCC) as their principal process for conversion because of the hydrocracker's relatively higher diesel yield and the superior quality of the diesel product. Additionally, many refineries are utilizing heavy oil processing technologies such as hydroprocessing and coking to convert short or long residues into transportation fuels.

FCC units produce a significant quantity of high-sulfur, low cetane number aromatic distillate, i.e., light cycle oil (LCO), which under the modern diesel quality specifications requires extensive hydrotreating or hydrogenation or hydrocracking to produce a diesel blending component. There are currently a number of high-pressure hydrotreating units that are specifically designed to upgrade FCC-produced LCO to a quality diesel fuel, which in addition to reducing sulfur content, substantially improve the cetane number of the resulting product stream, i.e., providing an increase of from 20 to 30 points.

In addition, increasing the severity of the FCC cracking conditions to maximize the production of lower molecular weight olefinic products from the FCC unit and oligomerizing these olefins has been practiced as an alternative method to produce high-quality synthetic diesel fuel.

Other solutions such as lowering the FCC naphtha endpoint have also been proposed to increase middle distillate production.

Production of middle distillate blending components from gasoline is well-known in the prior art. For example, WO 2012/076758 discloses a method for producing middle distillate fuel components from gasoline fuel component fractions by dimerization and/or oligomerization of olefins with carbon numbers ranging from 5 to 7.

Oligomerization reactions are defined as those which yield substances composed of molecules containing a few of one or more species of atoms or groups of atoms which are repetitively linked to each other. Catalysts used to oligomerize olefins include acid catalysts such as zeolites, non-zeolitic acid catalysts, nickel catalysts, and transition metal catalysts. Oligomerization is usually performed at temperatures above 200° C. and at pressures above 50 bar. In the method disclosed in WO 2012/076758, middle distillate hydrocarbons are produced after oligomerization/polymerization and fractionation of linear aliphatic hydrocarbons in the $C_9$-$C_{16}$ range corresponding to a normal boiling point in the range of from 165° C. to 290° C.

Alkylation of low carbon number olefins is a well known prior art process that produces alkylated gasoline blending components. There are numerous alkylation units installed in refineries throughout the world. The most common and widely used alkylation process utilizes a liquid acid, e.g., HF or $H_2SO_4$. Processes directed to solid acid alkylation utilizing superacids are also known in the prior art. A superacid, by definition, has an acidity equal to or stronger than 100% sulfuric acid. Another measure of superacidity is an acid whose Hammett acidity value is at least minus 12 or lower. Pure sulfuric acid has a Hammett acidity scale value of −12. Another widely accepted definition of a superacid that was proposed by Gillespie is any acid system that is stronger than 100% sulfuric acid, that is, $H_0 \geq 12$. Fluorosulfuric acid and trifluoromethanesulfonic acid are examples of Brønsted acids that exceed the acidity of sulfuric acid with $H_0$ values of about −15.1 and −14.1, respectively. However, it appears that currently no commercial units have yet been constructed to practice a superacid alkylation process.

The benefits of biofuels are numerous, including that they (a) are being produced from renewable feedstocks that can be grown by farmers, (b) can have a positive impact on local economic value chains, (c) may be produced in a sustainable manner, and (d) can be integrated relatively easily in the established infrastructure.

Biofuels are also seen as the only near-term direct substitute for fuels derived from crude oils because they can be delivered through existing logistics and can be combusted in conventional gasoline and diesel engines in either pure form or in a blend with relatively no or only minor changes. However, the propagation of biofuels has drawbacks and created challenges that remain to be addressed.

When judging the technical potential of biomass-derived biofuels it is important to differentiate between first and second generation biofuels. Feedstocks for first generation biofuels are based on their sugar content (e.g., sugar beet, sugar cane), starch (e.g., corn, wheat) or oil (e.g., rape seed, soybean, jatropha). These feedstocks can be converted into liquid fuels by means of conventional methods such as transesterification for production of fatty acid methyl ester (FAME), commonly referred to as 'Bio-Diesel', or fermentation of sugars and starch for production of ethanol. First generation biofuels are well established and have been in production in Europe and North America. A second generation of biofuels is based on cellulosic biomass, e.g., crops and plants. The quantities and types of feedstock, e.g., crop residues, tall grasses and wood, available for second generation biofuels are increasing significantly. The availability of cellulosic feedstocks will reduce the increasing competition for land between food crops and energy crops.

Oxygenate fuel additives are necessary for clean fuel combustion, i.e., reducing $NO_x$, CO and hydrocarbons released during the fuel's combustion. In the USA, the 1990 Clean Air Act required that reformulated gasoline (RFG) has to contain at most 2.7% oxygen content by weight. Recent regulations issued by European countries set the maximum limit of the oxygen content to 3.7% by 2013. The most economical oxygenates were methyl tertiary butyl ether (MTBE), methanol and ethanol. Unfortunately, MTBE is itself a pollutant, having an objectionable odor and taste and having been classified as a potential human carcinogen. To make matters worse, many gasoline storage tanks have developed leaks. MTBE is highly soluble in water and is low in biodegradability. Consequently, MTBE has polluted the ground water in many communities. Several U.S. states are phasing out the use of MTBE.

Many governments now are encouraging the use of alcohols, primarily ethanol. However, ethanol has some critical drawbacks as an oxygenate fuel additive or a fuel constituent, such as energy deficiency and corrosion. One of the greatest challenges to ramping up methanol/ethanol use in fuels is distributing it. Ethanol cannot be transported in the same pipelines used to distribute gasoline because it corrodes pipes and tubing. Although ethanol use reduces some forms of vehicular pollution, ethanol plants themselves are significant sources of emissions during the ethanol production process. In light of these problems with ethanol and MTBE, other alcohols such as butanol are emerging as a favored candidate to replace ethanol.

Butanol is an alcohol with the chemical structure $C_4H_9$—OH. It is more "fatty" in oxygenate than ethanol. Its longer hydrocarbon chain causes it to be relatively non-polar and it is more similar to gasoline than it is to ethanol. Butanol can be used as an oxygenate in reformulated gasoline for clean combustion to replace the two most widely used oxygenates, MTBE and ethanol. There are several reports on the use of gasoline-butanol blended fuel in different engines under different conditions. Some researchers concluded that the engine power level was maintained without any necessary modifications to the engine when the butanol concentration was below 20% by volume. Significant improvement to the overall fuel economy is observed in terms of reducing the total fuel energy consumption to produce unit crankshaft energy output. The initial engine test also indicated that the butanol blends offered measurable gains in thermal efficiency in line with the relative octane lift over the base gasoline. The butanol blended fuels were the lowest $NO_x$ emitters at fixed fuel oxygen content.

Butanol provides other advantages over ethanol and MTBE. Butanol has an energy content that is more comparable to that of gasoline than ethanol. The fuel-flow increase required for butanol is less than 10%, compared to 40% for ethanol. Butanol-gasoline blends have better efficiency and car mileage than gasoline-ethanol blends (Stefan Karl, "n-butanol as a 2nd Generation Biofuel for Compression Ignition- and Spark-Ignition Engine Application", Universität für Bodenkultur Wien, March 2008).

Table 1 provides a comparison of several properties of gasoline to those of other common blending additives.

TABLE 1

| Fuel | Energy Density MJ/Liters | Heat of Vaporization MJ/Kg | Research Octane No. (RON) | Motor Octane No. (MON) |
|---|---|---|---|---|
| Gasoline | 32.0 | 0.36 | 91-99 | 81-89 |
| n-butanol | 29.2 | 0.43 | 96-110 | 78-99.5 |
| Ethanol | 19.6 | 0.92 | 129 | 102 |
| Methanol | 16.0 | 1.20 | 136 | 104 |

Butanol tolerates water contamination. In blends with diesel or gasoline, butanol is less likely to separate from the fuel than ethanol, especially when the fuel is contaminated with water. Butanol is less corrosive than ethanol and therefore is more suitable for distribution through the existing infrastructure for gasoline than is ethanol. Butanols have reasonably high octane ratings and the branched forms of the $C_4$ alcohols provide even higher values.

The vapor pressures of butanols in gasoline blends are all lower than that of gasoline. Lower vapor pressure will lead to reduced fumes and lower VOC emissions to the atmosphere. Butanols are safer for use as oxygenates and can easily be added to conventional gasoline blends. The heat of vaporization of butanol is less than half that of ethanol. An engine running with a butanol blend is easier to start in cold weather than one running on ethanol or methanol blends.

Butanols can also be blended into conventional gasoline in higher proportions than ethanol because of its low vapor pressure. Currently, ethanol can be blended up to 10% v/v in European gasoline and 11.5% v/v in US gasoline. The DuPont/BP research on bio-butanol has demonstrated that a 16% v/v bio-butanol blend in gasoline does not compromise engine performance. As a practical matter, it will be necessary for one or more automotive manufacturers to provide a warranty guarantee before the butanol fuel blends can be commercialized.

The ebullated-bed reactor, which is a type of continuous stirred tank reactor (CSTR) for hydroprocessing hydrocarbon feedstocks, was commercialized in the 1960's and is described in U.S. Pat. Nos. 2,987,465 and 3,197,288. The ebullated-bed process comprises passing concurrently flowing streams of liquids or slurries of liquids and solids and gas through a vertically oriented cylindrical vessel containing catalyst. The catalyst is maintained in motion in the rising liquids and vapors and as dispersed through the fluid medium has a gross volume that is greater than the volume when the mass is stationary. This technology has been utilized in the upgrading of heavy liquid hydrocarbons and the conversion of coal to synthetic oil.

For hydroprocessing applications, a mixture of hydrocarbon liquid and hydrogen is passed upwardly through a bed of catalyst particles at a rate at which the particles are forced into motion. The catalyst bed level is controlled by a recycle liquid flow so that at steady state, the bulk of the catalyst does not rise above a predetermined level in the reactor.

Vapors, along with the liquids which are being reacted, pass through the upper surface of the catalyst particles into a substantially catalyst-free zone and are removed from the upper portion of the reactor.

In the traditional ebullated-bed process, substantial amounts of hydrogen gas and light hydrocarbon vapors present rise through the reaction zone into the catalyst-free zone. Liquid is both recycled to the bottom of the reactor and removed from the reactor as net product from this catalyst-free zone. Vapor is separated from the liquid recycle stream before being passed through the recycle conduit to the suction side of the recycle pump. The recycle pump, also referred to as the ebullating pump, maintains the expansion or ebullation of the catalyst at a constant and stable level. Gases or vapors present in the recycled liquid materially decrease the capacity of the recycle pump and also reduce the liquid residence time in the reactor and limit hydrogen partial pressure.

Reactors employed in a catalytic hydrocracking process with an ebullated-bed of catalyst particles are designed with a central vertical recycle conduit which serves as the downcomer or down flow for recycling liquid from the catalyst-free zone above the ebullated catalyst bed to the suction side of the recycle pump to recirculate the liquid through the catalytic reaction zone. Alternatively, the ebullating liquid hydrocarbon stream can be obtained from a vapor separator located downstream of the reactor or it can be the bottoms of an atmospheric stripper. The recycling of liquid serves to ebullate the catalyst bed, maintain temperature uniformity through the reactor and stabilize the movement of the catalyst bed within a predetermined range or height in the reaction vessel.

Catalyst bed expansion in an expanded bed reactor is another important factor in the operational control of the ebullated-bed reactor. In the process, the expansion of the bed is controlled by changing the reactor recycle pump speed to vary the volumetric fluid flow rate. The bed is provided with a number of bed level detectors or sensors and an additional detector for alerting operating personnel to an abnormally high bed interface level. The interface level can be determined by means of a density detector comprising a radiation source positioned in the interior of the reactor and a detection source in the reactor wall. Raising or lowering the bed interface level changes the density of the radiation transmitted from the radiation source to the detector.

As a result of the growing demand for middle distillate products, the problem faced by petroleum refiners is how to selectively increase their production of middle distillate fuel components.

SUMMARY OF THE INVENTION

This problem is resolved and other advantages are provided by the present process in which hydrocarbon compounds suitable for use as gasoline blending components are converted into middle distillate fuel blending components suitable for use as aviation and diesel fuels.

The invention broadly comprehends a process in which olefinic compounds are hydrated to produce blending components for middle distillates such as diesel. Specifically, an olefinic naphtha feedstream having a carbon number ranging from 7 to 14 is hydrated thereby converting the olefins to the corresponding mixed alcohols as shown in the following reaction scheme:

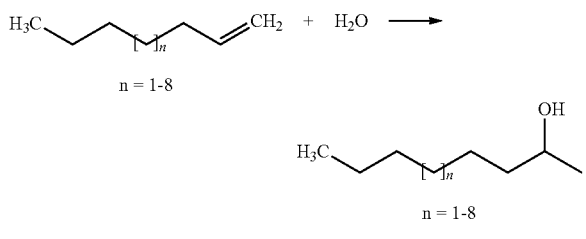

As shown in FIG. 1, the alcohol product stream has an average boiling point that is about 28° C. higher than the corresponding olefinic naphtha stream, thus shifting it into the diesel boiling point range.

A particular advantage of the present process is the ability to separate the longer chain alcohols from the aqueous reactant mix. The $C_7$ heptanol has a solubility value of 0.0008 mol/100 g of $H_2O$ at 1 atm and 25° C. The $C_8$ and longer chain alcohols produced are considered immiscible with water. They are also less dense than water permitting the water to be readily separated by gravity settling. The $C_7$ to $C_{14}$ alcohols can easily be recovered by fractionation for transfer to the diesel fuel blending components pool.

It is to be noted that when isolated, some of the longer chain alcohols are solids at ambient conditions; however, they are readily solubilized in the shorter chain alcohols. For example, naphthalene, a two-ring condensed aromatic, is a solid at room temperature, but is in solution in diesel fuel under ambient conditions.

Referring now to FIG. 2 which shows the cetane number of paraffins, olefins and alcohols as a function of carbon number. It is noted that the average cetane number of olefins in the $C_8$ to $C_{14}$ range of carbon numbers is about 2 points higher than the corresponding alcohols produced by the hydration reaction. This relatively small difference can be accounted for by the presence of other blending components having higher cetane numbers that are present or introduced into the diesel blending pool. The benefit seen by the refiner is the overall increase in the volume of the diesel pool provided by the addition of the higher boiling point alcohols.

Referring to FIG. 3, as will be seen from the plot of the specific gravity values for paraffins, olefins and alcohols in the $C_7$ to $C_{14}$ range, the alcohols have a higher density compared to the corresponding olefins and thus a reduced volume.

Relative lubricity is a measure of by how much the friction between two surfaces is reduced when a lubricant is placed between them. By adhering to the surface of a metal, for example, a lubricant molecule can reduce the friction and wear occurring during moving contact with another material. Tests to determine lubricity are often performed by monitoring the wear that is caused when surfaces slide across each other. A surface with the smaller "wear scar" is considered to have a higher lubricity.

In the operation of an internal combustion engine, the fuel serves as part of the engine's lubrication system. Fuels with alcohols provide better lubrication than fuels without them. The structure of the protective lubricant layer or film formed on surfaces is influenced by the structure and functional groups of the compound(s) forming the film. For linear hydrocarbons, alcohols are better lubricants than alkanes or alkenes. This is because alcohols are more polar than alkanes and alkenes, and their polarity leads to the formation of stronger bonds with the surface that is lubricated, thereby resulting in less of a wear scar. In addition, alcohols provide better lubricity with increasing chain length. In general, the so-called "fatty alcohols" from $C_8$ to $C_{11}$ are described as oily liquids. Similarly, longer-chain alcohols exhibit lower corrosion activity than shorter-chain, e.g., $C_1$ to $C_5$ alcohols.

The olefinic naphtha feedstream for use in the integrated process of the invention can be derived from any suitable unit operation that is conveniently available within the battery limits of the refinery. For example, the source of the hydration process feedstream can be an FCC unit, a thermal cracking unit, or a combined feed from these units. The types of thermal cracking unit operations from which suitable olefin streams can be derived are delayed or fluid coking units, visbreaking units, conventional thermal cracking units, pyrolysis units, steam cracking units, and other cracking processes that do not employ hydrogen. As will be apparent to one of ordinary skill in the art, not all of these unit operations are likely to be found within a single refinery. To the extent that two or more such operations are available to provide an olefinic paraffin feedstream to the hydration process of the invention, the choice, or choices, can be based on the physical proximity of the source, the quality of the source and the presence or absence of other constituents in the feeds, including their respective carbon chain lengths within the desired ranges of $C_7$ to $C_{14}$ that are required to form the corresponding alcohols having boiling points in the range of middle distillate fuel blending components.

A suitable catalyst for use in the process is a soluble homogeneous compound or a solid heterogeneous compound selected from resins and amorphous or structured metal oxides having Lewis or Bronsted acid sites. The metal oxides can be selected from IUPAC Groups, 4-10, 13 and 14, which correspond to Groups IIIA, IVA, IVB, VB, VI, VII and VIIIB of the Periodic Table. Catalyst particles can range from 0.15 mm to 6 mm, or $\frac{1}{16}^{th}$ to $\frac{1}{4}$ inch, with a preferred surface area in the range of from 30 to 100 $m^2/g$, and a preferred pore diameter of from 200 to 300 angstroms. A key characteristic of the catalyst is that it possesses Lewis or Bronsted acid sites.

The following commercially available catalysts are representative of those which have been found to be suitable for use in the hydration reaction. The Dow Chemical Company's AMBERLYST 15 is a standard macroporous catalyst with excellent lifetime and good conversion rate with a high physical and osmotic pressure resistance; and AMBERLYST 70, another macroporous catalyst that exhibits high thermal stability at 180° to 200° C. and is well suited for SBA and IPA production. Chemra GmbH of Trier, Germany sells TREVER®ILYST CAT400 which exhibits thermal stability up to 190° C. (375° F.) and is physically very stable; and TREVER®ILYST CAT410 which exhibits thermal stability up to 190° C., has a long life time due to its specific porosity, and can also be used in alkylation reactions or where $AlCl_3$ or $BF_3$ has to be replaced.

A dual-phase catalyst of the type disclosed in U.S. Pat. No. 8,558,036 can also be used to advantage in the process of the invention for the production of mixed alcohols from mixed olefins. The dual phase catalyst system comprises a water soluble acid catalyst selected from phosphotungstic acid hydrate and tungstosilicic acid hydrate and a solid acid catalyst that is insoluble in water, and is capable of hydrating the mixed olefins without the separation of the mixed olefins prior to their contact with the dual phase catalyst system. An advantage of the dual phase catalyst system that it is capable of converting the mixed olefins into the mixed alcohols at a conversion rate that is greater than that of the water soluble acid catalyst or the solid acid catalyst. The disclosure of U.S. Pat. No. 8,558,036 is incorporated herein by reference.

When a liquid acid is employed, contactor reactors of the type used in liquid acid alkylation processes can be used to advantage.

In the process of the present disclosure, the olefin hydration zone can operate at a pressure in the range of from 10-100 $Kg/cm^2$, preferably from 30-80 $Kg/cm^2$, and more preferably from 50-70 $Kg/cm^2$, and at a temperature of 25° C. to 300° C., preferably from 100° C. to 250° C., and preferably from 130° C. to 200° C. The liquid recycle-to-feed oil ratio can be in the range of from 1 to 30, preferably from 2 to 20, and more preferably from 4-10. The liquid space velocity can be from 0.01-10.0 volume of feed per hour per volume of reactor (V/h/V), is preferably 0.05-5.0, and more preferably from 0.1-1.0. The water-to-olefin ratio is in the range of from 1:1 and 8:1.

It has been found that in the olefin-to-alcohol process, the olefin conversion rate is a function of the feedstock used, the catalyst(s) employed, and the temperature and pressure of the reactor. Where the conversion rate is low, the unconverted olefinic feedstock must be recycled to the reactor or processed in a series of reactors in order to maintain process efficiency. From a thermodynamic point of view, high pressures and low temperatures generally favor the olefin-to-alcohol conversion process. In some embodiments, the olefin-to-alcohol conversion rate can require a recycle-to-fresh feed ratio of about 97:3, or a ratio of about 4:1, or a ratio of about 1:1. Capital costs for multiple reactors must be balanced against the liquid hourly flow requirement/demand for the alcohol.

Suitable apparatus and reactors for conducting the acid-catalyzed olefinic hydration of the feedstream are conventional and known in the art, and include fixed-bed and continuously stirred tank reactors (CSTR).

A suitable apparatus to produce transportation fuel-quality blending alcohols from olefinic streams includes an ebullated-bed reactor with associated upstream and downstream major equipment. Ebullated-bed reactors have been found to be particularly well suited for the olefin hydration reaction of the present invention which has a relatively low conversion rate and associated large recycle requirement. An ebullated-bed reactor is a specific type of CSTR reactor because of the recycle of the unconverted material. For the practice of the present process, the external recycle mode of operation provides advantages that will be described in more detail below.

The ebullated-bed reactor can be operated as a two- or three-phase fluidized bed reactor that is back-mixed in terms of reactor liquid composition of the CSTR and the motion of the catalyst particles. The liquid feed in the two-phase system and gas in the three-phase system enter the reactor at the bottom and are distributed across the bed by a distributor and grid plate.

The catalyst particles are fluidized in the reactor by the upward lift of the fresh liquid reactants and the recycle liquid which is needed to maintain and adjust the ebullation. Liquids and vapors are either separated internally, e.g., by internal recycle, or externally by external recycle.

The unconverted olefins are separated in a separation vessel alone or optionally in combination with a flash vessel downstream of the reactor, and are recovered and recycled to the reactor in the liquid-phase via the ebullating pump. The unconverted water is separated in the same separation vessel and recycled to the reactor through the ebullating pump. The alcohol is collected as a liquid product stream from the separation vessel. The use of an ebullated-bed reactor increases the overall process efficiency, because the unconverted feedstock is recycled to the reactor.

In a preferred embodiment, the heterogeneous solid catalyst is continuously removed, regenerated and recycled to the ebullated bed reactor. A typical catalyst handling system consists of three sections: a fresh catalyst handling section, a section for the periodic, for example, daily, addition/withdrawal of catalyst, and a spent catalyst handling section. Fresh catalyst is typically introduced into the reactor vessel through a high-pressure transfer vessel. Spent catalyst is withdrawn from the reactor and moved to another high-pressure transfer vessel where it is cooled and washed and then transferred to a spent catalyst storage vessel for regeneration. In accordance with known methods, some proportion of the spent catalyst may be withdrawn from the system and replaced with new catalyst in order to maintain the level of activity required to achieve the desired rate of conversion in the reaction.

If present, the homogeneous soluble catalyst is a component of the liquid mixture in the reactor and the heterogeneous solid catalyst is fluidized and kept in turbulent suspension, i.e., it is ebullated, in the reactor by the upflow of the liquid mixture. The fluidized nature of ebullated-bed reactors permits the easy removal of spent catalyst and prevents the plugging problems that are common in fixed-bed reactors. The opportunity for daily catalyst addition/withdrawal provides flexibility and longevity to this unit operation when compared to alternative processes, e.g., to a fixed-bed reactor.

A slurry-bed reactor is preferred where a homogeneous catalyst is used alone. The ebullated-bed reactor requires solid heterogeneous catalysts. However, homogeneous catalysts can be used together with a heterogeneous catalyst. The use of homogeneous and heterogeneous catalysts in combination is commercially practiced in the operation of residue hydrocracking operations utilizing the ebullated-bed reactor. The optional homogeneous catalyst is typically added in the ppm by weight (ppmw) range and does not detract from the activity of the heterogeneous catalyst. The preferred range for catalyst particles is from 1.5 mm to 6 mm (¹⁄₁₆ inch to ¼ inch), the preferred size being at the lower end of the range, e.g., 1.5 mm (¹⁄₁₆ inch). The surface area of the catalyst is in the range of from 10 to 1000 $m^2/g$, preferably from 20 to 500 $m^2/g$ and more preferably 30 to 100 $m^2/g$. The pore diameter of the catalyst can be in the range of from 10 to 500 angstroms, is preferably from 100 to 400 angstroms, and most preferably is from 200 to 300 angstroms.

A variety of acids can be used as catalysts in the hydration process. It will be understood by those of ordinary skill in the art that the use of liquid acids will incur additional equipment cost, e.g., acid resistant vessels, mixing equipment, valves and piping, and handling expenses to comply with environmental regulations and concerns. In view of these considerations, it may be preferred to use a liquid acid in a type of reactor specifically adapted for such reactive materials, e.g., a contactor-type reactor used with liquid HF or $H_2SO_4$ in alkylation processes, and such acid catalyzed reactions are practiced commercially. When the process is to be practiced in existing conventional equipment, e.g., ebullated-bed reactors, it may be most preferred to operate with heterogeneous catalysts alone, and without the addition of a liquid acid.

The homogeneous catalyst is present in the aqueous phase of the system where it is easily separated and removed from the system in the manner described below. With this step, there will be no significant carryover of the homogeneous catalyst to the hydrocarbon reaction product stream which is essentially immiscible with water. Since the homogeneous catalyst is typically added in the ppm by weight range, it can be added to the feedstock continuously, based upon operating parameters that are readily determined by one of ordinary skill in the art. The amount and timing of the addition of the homogeneous catalyst is determined empirically by analysis of the feedstream for the olefin content and of the product stream, or experimentally in pilot plant or laboratory-scale runs using samples of representative feeds and reactor conditions.

When sulfuric acid is used, the reaction mechanism proceeds with the conversion of the alkenes to yield alkyl sulfate esters, which are then hydrolyzed to regenerate sulfuric acid with the release of ethanol. Although the sulfuric acid can be recovered, the economics may not favor this additional step.

BRIEF DESCRIPTION OF THE DRAWINGS

The invention will be described in further detail below and with reference to the attached drawings in which the same numerals are used to identify the same or similar components, and where.

DETAILED DESCRIPTION OF THE INVENTION

An embodiment of the process and a system for its practice in accordance with the present invention will be described with reference to FIG. 4 which schematically depicts an olefin hydration zone comprising an ebullated-bed reactor (20) fitted with a catalyst feed line (22) for introduction of fresh and/or regenerated catalyst and a catalyst withdrawal line (24) for removing spent catalyst from the ebullated-bed reactor. It will be understood that reactor (20) is also provided with suitable valves, gauges and controls which are well known and conventional in the art, and which are omitted in the interest of clarity for the purpose of describing the relevant features and limitations of the present invention. In view of the relatively low conversion rate of the hydration reaction, the system can include a plurality, e.g., up to 6 ebullated-bed reactors in order to meet product requirements.

Figure 1:
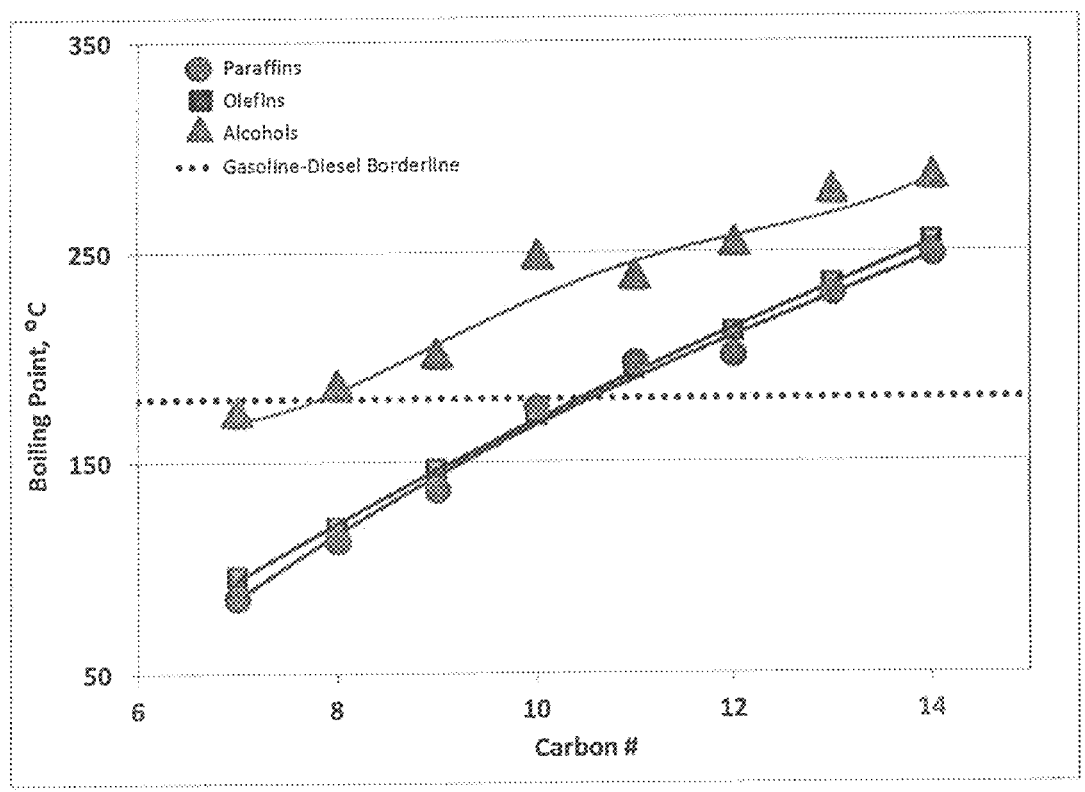
FIG. 1 is a chart illustrating the typical variation in boiling points of olefins, paraffins and alcohols in relation to their carbon number.
Figure 2:
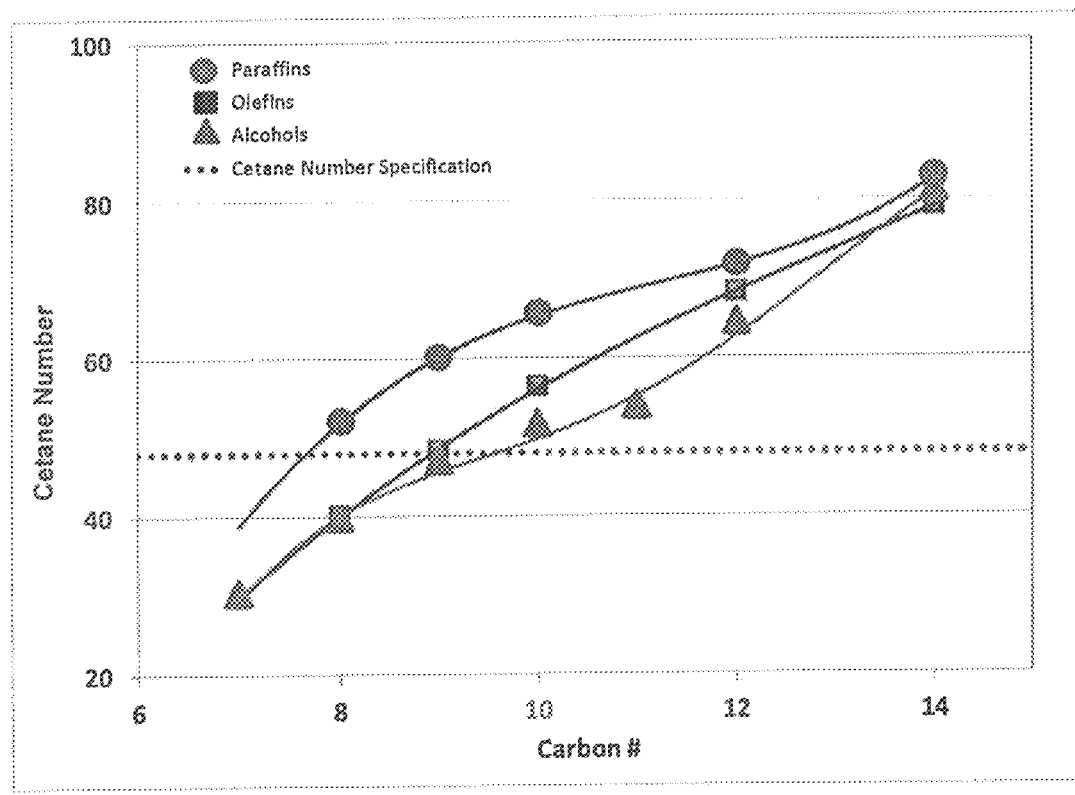
FIG. 2 is a chart illustrating the typical variation in cetane numbers of olefins, paraffins and alcohols in relation to their carbon number.
Figure 3:
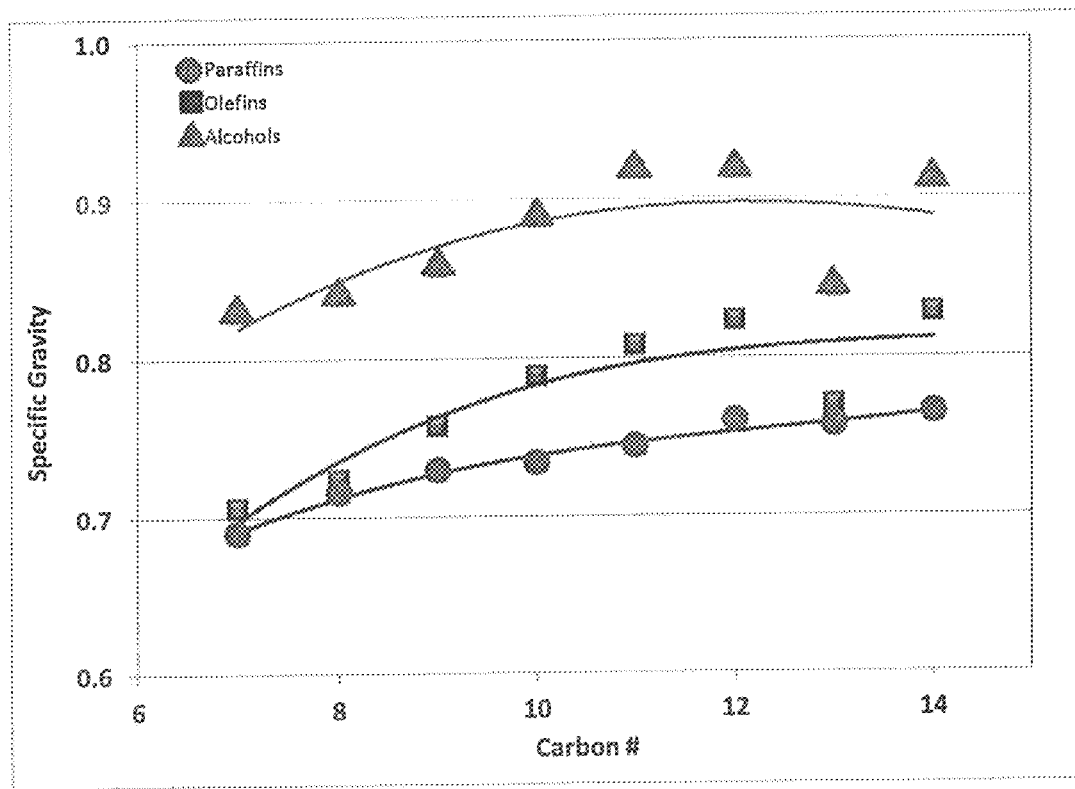
FIG. 3 is a chart illustrating the typical variation in specific gravity of olefins, paraffins and alcohols in relation to their carbon number.
Figure 4:
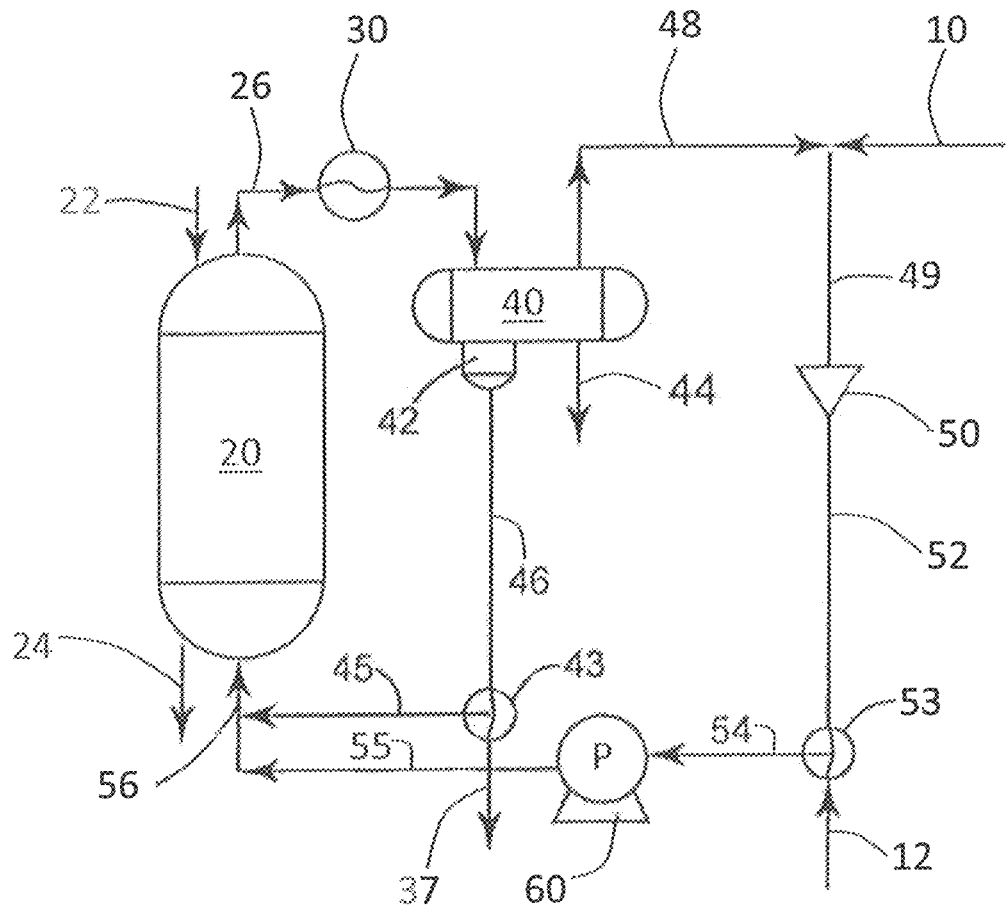
FIG. 4 is a schematic diagram illustrating an embodiment of a system suitable for the practice of the process of the present invention.

The other principal elements of the apparatus and system shown in the embodiment of the process illustrated in FIG. 4 are a heat exchanger (30), either air or liquid cooled to reduce the temperature of the reactor effluent product stream (26) from the reactor (20); a separator (40) from which the alcohol product stream (44) is recovered; a recycle stream

(48) comprising unconverted olefins and other reaction by-products and an aqueous stream (46) that passes through an outlet in settling chamber (42) formed in a lower portion of the separator (40); a mixer (50) which receives the combined recycle stream (48) from separator (40) and the fresh paraffinic olefin stream (10) as the combined mixed feed stream (49). Ebullating pump (60) receives the mixed fresh and recycle olefin feed (52) from mixer (50), along with a predetermined volume of make-up water (12) that is input to the pump (60) as the mixed reactant stream (54) via control valve (53) and discharged as pressurized stream (55). All or a portion of recycle water stream (46) is recycled back to the reactor through line (45) via control valve (43) and enters as mixed hydrocarbon/water stream (56). Depending upon the composition of the aqueous stream (46) recovered from the settler (42) in separator (40), a portion of aqueous stream (46) can be decanted from the system via control valve (43) and line (37).

Where two feedstreams are combined in part, three-way control valves, e.g., (43) and (53), with associated instrumentation (not shown) are provided to permit the proper ratio and by-pass and discharge of water from the system. As will be understood by one of ordinary skill in the art, the functions of monitoring the composition of the feedstreams and adjustment of the various control valves can be automated with the use of commercially available sensors, programs, microprocessors and controllers.

Due to the chemical equilibrium point of the hydration reaction, as previously noted, the conversion rate is relatively low and the unconverted material is recycled to the reactor. The product stream from the separator is fractionated and the distillate range product recovered is then sent directly to the distillate pool. The separated unreacted gasoline fraction is preferably recycled to the reactor for hydration of the unconverted olefins. The aqueous solution recovered from the separator (40) can contain a variety of by-products including the highly water soluble lower alcohols produced in the hydration reaction, and it may be desirable and necessary to further process the decanted aqueous stream (37).

The system can include one or more flash vessels to treat the effluent product stream to recover light products produced as reaction by-products and/or carried over from the fresh and/or recycled feeds. A flash vessel can be installed upstream or downstream of heat exchanger (30) or downstream of the separator (40).

The practice of the integrated refinery process will be described further with the assumption of a steady-state condition following start-up of the system. The paraffinic olefin-containing feedstock (10) is preferably recovered from an FCC unit and/or a thermal cracking unit (not shown) that is conveniently located with respect to the reactor and within the battery limits of the refinery. A suitable feed is FCC naphtha boiling in the range of from 36° to 240° C. The feedstock is preferably free of metal compounds, or substantially so. The feed is also low in sulfur- and nitrogen-containing hydrocarbons, e.g., with sulfur in the range of from 10 to 20 ppm and nitrogen in the range of from 10 to 10,000 ppm.

In those refinery systems where the FCC unit has an upstream hydrodesulfurization unit, e.g., a VGO pretreatment unit, or the refinery processes hydrocracker bottoms, the sulfur and nitrogen levels will be very low. Use of feedstocks with low levels of these undesired compounds represent a preferred embodiment so that the diesel range blending components will enhance the characteristics of the pool. Lowering the values of these undesired constituents will also prolong the life of the solid catalyst(s). A cleaner feedstock will result in a longer cycle life for the catalyst. If there is no hydrodesulfurization unit and the FCC unit processes straight run (SR) VGO, the sulfur and nitrogen levels will be higher and the useful life of the catalyst will be reduced.

The following examples are illustrative of the practice of the process of the invention.

EXAMPLE 1

A coker naphtha feed having a carbon number in the range of from 7-11 with the composition set forth in Table 2 was subjected to hydration at 180° C. over a resin catalyst available from Signa Aldrich under the brand name AMBERLITE® 15. Upon hydration at full conversion, the average boiling point of the coker naphtha fraction had been increased by 60° C. from 137° C. to 197° C.

TABLE 2

| C# | Paraffinic Naphthenes | Olefins | Aromatics |
| --- | --- | --- | --- |
| 8 | 16.27 | 11.55 | 6.97 |
| 9 | 15.92 | 9.15 | 8.38 |
| 10 | 11.48 | 5.46 | 5.66 |
| 11 | 5.81 | 3.36 | 0.00 |
| | 49.5 | 29.5 | 21.0 |

EXAMPLE 2

Figure 5:
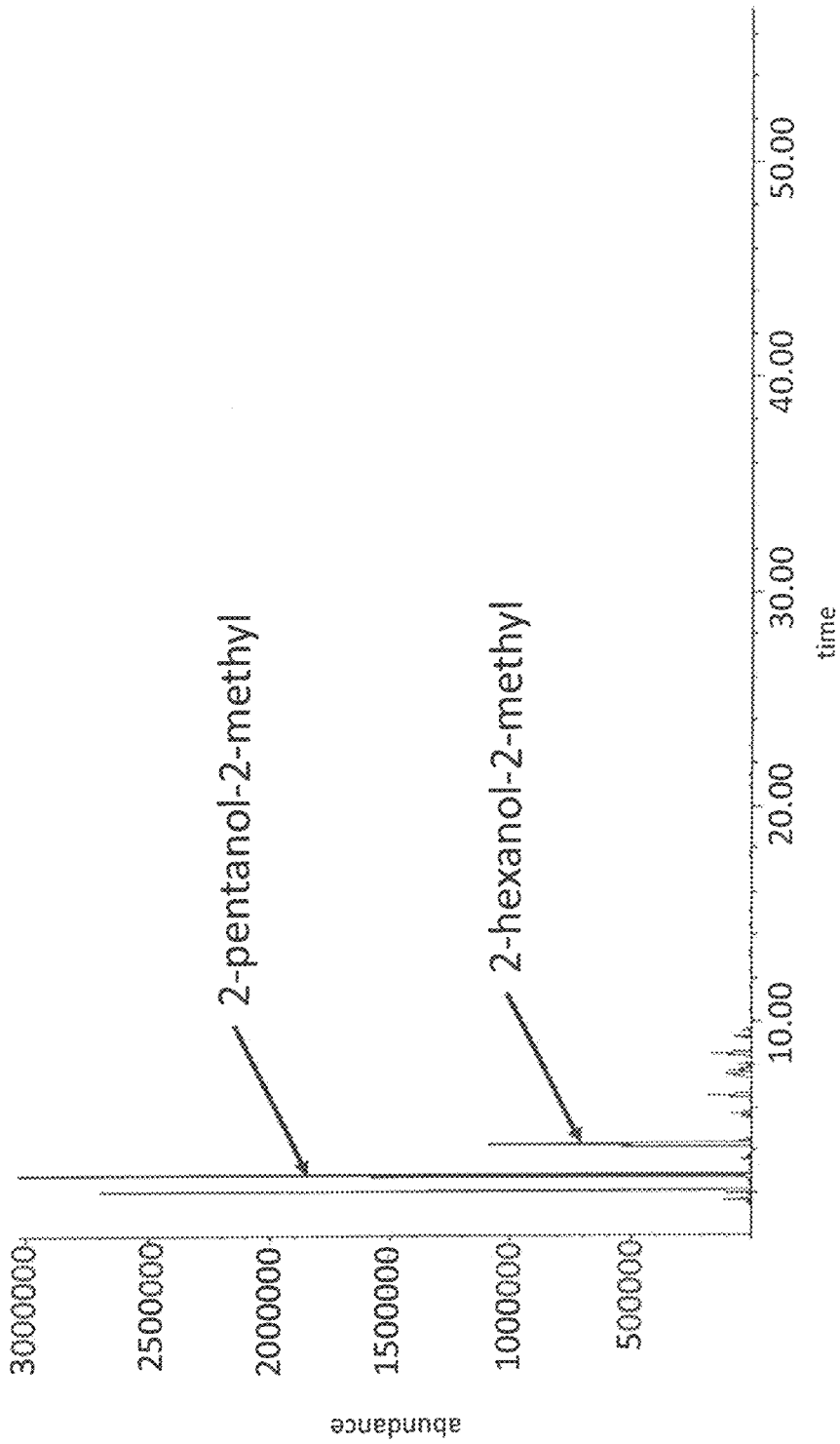
FIG. 5 is an expanded version of the relevant portion of a chromatogram showing the results of the chromatographic analysis of a reaction product produced by the present process.

Fifty cc of FCC gasoline was added to a one-liter round bottom flask and cooled in an ice bath for about three minutes; 50 cc of 75% sulfuric acid was then slowly added to the cooled gasoline while stirring the mixture with a glass rod. After all of the acid was added, the mixture was stirred until a single homogeneous layer formed. The mixture was allowed to stand in the ice bath for another 5 minutes, after which 50 cc of cold water was added. The mixture separated into two layers, the upper layer containing the hydrated FCC gasoline, and the lower layer containing mainly the aqueous sulfuric acid. The original FCC naphtha feedstock and the treated product were analyzed using the PIONA method, the results of which are tabulated in Table 3. The PIONA method only analyzes fractions boiling up to 180° C. As seen in this range of naphtha, about 25 W % of olefins are converted. An increase in aromatics and naphthenes is also shown by the PIONA analysis. However, because the PIONA data may not reflect the true increase in aromatics and naphthenes, the product sample was analyzed by gas chromatographic mass spectrometry (GC-MS) in order to confirm the formation of alcohols. Referring to FIG. 5, it can be seen from the detail of the relevant portion of the chromatogram of the sample that 2-pentanol-2-methyl and 2-hexanol-2 methyl were present, thus confirming the formation of alcohols.

TABLE 3

| | FCC Naphtha (W %) | FCC Naphtha Treated (W %) |
| --- | --- | --- |
| Paraffins | 28.5 | 28.6 |
| Aromatics | 31.7 | 38.7 |
| Olefins | 33.7 | 25.2 |

TABLE 3-continued

| | FCC Naphtha (W %) | FCC Naphtha Treated (W %) |
|---|---|---|
| Naphthenes | 5.9 | 7.3 |
| Unidentified | 0.2 | 0.1 |
| | 100 | 100 |

Figure 6:
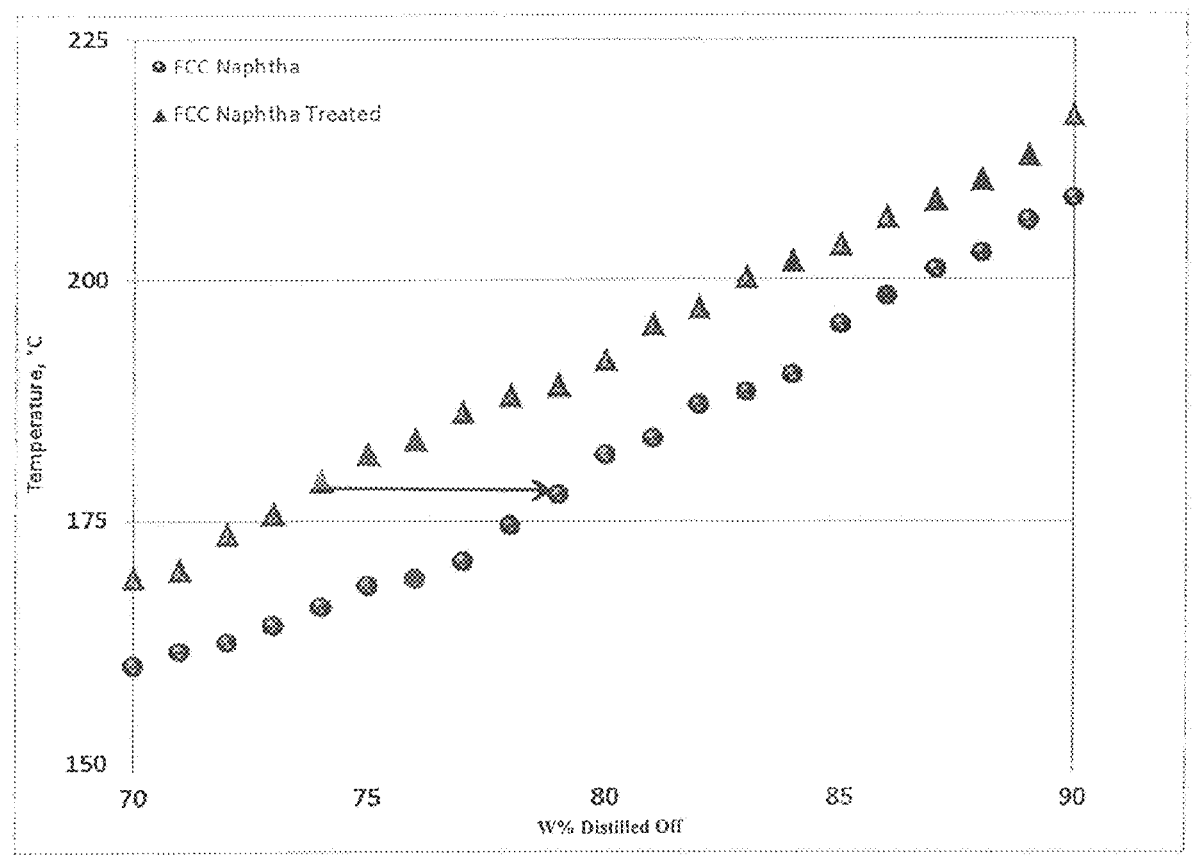
FIG. 6 is a graphic plot of temperature versus weight percent of material distilled off for the starting FCC naphtha sample and the treated FCC naphtha based on simulated distillation data.

The FCC naphtha feedstock and treated products were also analyzed using the simulated distillation methodology of ASTM Method D2887. As seen in FIG. 6, a major increase in boiling points is observed indicating the formation of alcohols. The simulated distillation data shows that the FCC naphtha feed and the treated FCC naphtha contain 79 W % gasoline and 74 W % gasoline, respectively, indicating a 5 W % shift from the gasoline range into the middle distillate range.

The process of the invention can advantageously be installed downstream of an FCC or other cracking unit(s). Since the main objective is to convert FCC naphtha a into middle distillate range material, the use of mid-range and heavy naphthas are preferred, although the process can also be used to hydrate full range naphtha.

Various embodiments have been described above and in the attached figures and further modifications to the process and system will be apparent to those of ordinary skill in the art from this description and the scope of protection accorded the invention is to be determined by reference to the claims.

The invention claimed is:

1. A process for converting olefins boiling in the gasoline range to their corresponding alcohols boiling in the middle distillate range comprising:
   a. introducing water and an olefinic feedstock having carbon numbers ranging from 7 to 14 that is derived from a unit operation selected from the group of unit operations consisting of an FCC unit, one or more thermal cracking units, and their combination, into a recycle conduit to form a combined olefin and water stream;
   b. passing the combined olefin and water stream through an ebullated bed recycle pump to pressurize the combined stream;
   b. introducing the pressurized combined stream into an olefin hydration zone that comprises at least one ebullated bed reactor that contains at least one hydration catalyst;
   c. reacting the olefins with the water in the pressurized combined stream in the presence of the at least one hydration catalyst in the olefin hydration zone to produce reaction products comprising alcohols, dimers of olefins, and oligomers of olefins;
   d. passing a reaction product stream from the olefin hydration zone to a separation zone to separate any unreacted materials from the reaction product stream;
   e. recycling the unreacted materials to the olefin hydration zone via the recycle conduit for combination with the water and the olefinic feedstock of step (a);
   f. recovering the separated hydration reaction product stream as a middle distillate blending product; and
   g. transferring the middle distillate blending product to a diesel fuel blending pool and/or an aviation fuel blending pool.

2. The process of claim 1, wherein the olefin hydration zone operates at a pressure in the range of from 10 to 120 kg/cm².

3. The process of claim 1, wherein the olefin hydration zone operates at a temperature in the range of from 25° C. to 300° C.

4. The process of claim 1, wherein the olefin hydration zone comprises a plurality of ebullated bed reactors containing one or more heterogeneous catalysts.

5. The process of claim 1, wherein the olefin hydration zone comprises one reactor containing an oil-soluble homogeneous catalyst.

6. The process of claim 1, wherein the weight ratio of recycled unreacted olefinic feedstock-to-fresh olefinic feedstock is about 97 to 3.

7. The process of claim 1, wherein the liquid space velocity of the olefinic feedstock is from 0.01 to 10.0 volume of feed per hour per volume of reactor (V/h/V).

8. The process of claim 1, wherein the water-to-olefinic feedstock ratio is in the range of 1:1 to 8:1 by weight.

9. The process of claim 1, wherein the catalyst is an oil-soluble homogeneous or a solid heterogeneous catalyst that is selected from ion-exchange resins and amorphous or structured metal oxides.

10. The process of claim 1, wherein the catalyst includes a metal selected from IUPAC groups 4-10, 13 and 14.

11. The process of claim 1, wherein the catalyst particle size is in the range of from 0.15 to 6 mm.

12. The process of claim 1, wherein the surface area of the catalyst is in the range of from 10 to 1000 m²/g.

13. The process of claim 1, wherein the pore diameter of the catalyst is in the range of from 10 to 500 angstroms.

14. The process of claim 1 in which the olefinic feedstream is derived from a thermal cracking unit selected from the group consisting of delayed coking units, fluid coking units, visbreaking units, pyrolysis units, stream cracking units and conventional thermal cracking units.

15. The process of claim 1, wherein the middle distillate blending product from the hydration process has a cetane number equivalent to, or 2 points lower than the cetane number of the olefinic feedstock.

16. The process of claim 1, wherein the hydration process increases the boiling point of the original olefin-containing feedstock from temperatures in the gasoline range to a hydration reaction product stream with boiling point temperatures in the diesel range.

17. The process of claim 1, where the hydration process products exhibit improved lubricity compared to the olefinic starting materials.

18. The process of claim 1, where the hydration process products have a specific gravity that is greater than the specific gravity of the feedstock.

19. An integrated refinery system for the production of alcohols boiling in the middle distillate range comprising:
   a. at least one ebullated bed reactor comprising a feed inlet, an effluent product outlet, a fresh catalyst inlet, a catalyst withdrawal outlet, and a hydration zone containing at least one hydration catalyst,
   the feed inlet of each ebullated bed reactor being in fluid communication with at least one refinery unit operation that is a source of an olefinic naphtha feedstock having carbon numbers in the range of from 7 to 14,
   the fresh catalyst inlet being located proximate the top of the ebullated bed reactor and in communication with a catalyst regeneration zone,
   the effluent product outlet of each ebullated bed reactor being in fluid communication with a separator for separating an alcohol-containing product stream, and the catalyst withdrawal outlet being located proximate the bottom of each ebullated bed reactor and in communication with an inlet of the catalyst regeneration zone;
b. an ebullated bed recycle pump in fluid communication with a recycle conduit and the feed inlet of the reactor;
c. the separator comprising
   a separator inlet for receiving effluent product stream from each ebullated bed,
   a separator product outlet for discharging an alcohol product stream, and
   a separator recycle outlet in fluid communication with the recycle conduit;
d. the recycle conduit being in fluid communication with the separator recycle outlet and the ebullated bed recycle pump, the conduit receiving and combining effluent from the separator recycle outlet, fresh olefinic naphtha and water for introduction to the ebullated bed recycle pump.

20. The system of claim 19 which includes a compressor having an outlet in fluid communication with the inlet of the recycle pump and an inlet for receiving the recycle stream from the separator and fresh olefinic naphtha feedstock.

21. The system of claim 19 in which at least a portion of the aqueous solution from the separator is recycled to the ebullated bed reactor.

22. The system of claim 21 in which a portion of the aqueous solution from the separator is discharged from the system.

23. The system of claim 19 in which fresh water enters the recycle conduit after the fresh and recycled feeds are combined upstream of the recycle pump.

24. The system of claim 19 which includes a heat exchanger upstream of the separator inlet for reducing the temperature of the effluent product stream.

25. The system of claim 19 which includes a flash vessel in fluid communication with the effluent product outlet of the reactor and having an outlet for recovery of light components removed from the effluent product stream by the flash vessel.

* * * * *